US006793819B2

(12) United States Patent
Glenwright et al.

(10) Patent No.: US 6,793,819 B2
(45) Date of Patent: Sep. 21, 2004

(54) AIRTIGHT WASTE SOLUTION SAMPLING APPARATUS

(75) Inventors: Thomas B. Glenwright, Webster, NY (US); Warren R. Smith, Webster, NY (US); Brian L. Spencer, Brockport, NY (US); James F. Graf, Jr., Webster, NY (US)

(73) Assignee: Xerox Corporation, Stamford, CT (US)

( * ) Notice: Subject to any disclaimer, the term of this patent is extended or adjusted under 35 U.S.C. 154(b) by 361 days.

(21) Appl. No.: 10/053,823

(22) Filed: Jan. 24, 2002

(65) Prior Publication Data

US 2003/0136723 A1 Jul. 24, 2003

(51) Int. Cl.[7] ............................ B01D 41/00; G01N 1/10

(52) U.S. Cl. ................. 210/269; 73/863.71; 73/863.72; 73/863.83; 73/863.84

(58) Field of Search ................................ 210/260, 269; 73/863.21, 863.71, 863.72, 863.81, 863.83, 863.84, 863.85, 863.86

(56) References Cited

U.S. PATENT DOCUMENTS 4,009,617 A * 3/1977 Johnson ................... 73/863.84

FOREIGN PATENT DOCUMENTS

JP 55142235 A * 11/1980 ............. 73/863.83

* cited by examiner

*Primary Examiner*—Robert A. Hopkins
(74) *Attorney, Agent, or Firm*—Tallam I. Nguti

(57) ABSTRACT

An airtight sampling apparatus for effectively and accurately sampling a waste solution including volatile organic compounds (VOC's) from a main waste solution conduit having a first pressure P1, is provided. The airtight sampling apparatus includes (a) a waste solution sampling conduit having a first end and a second end; (b) an input check valve connecting the first end of the waste solution sampling conduit to the main waste solution conduit; (c) an actuatable waste solution containing and discharge cylinder assembly having a first end and a second end connected to the second end of the waste solution sampling conduit; (d) an attachable and removable airtight sample holding container; and (e) a pressure adjustable output valve for coupling to the airtight sample holding container, the pressure adjustable output valve being located between the input check valve and the second end of the waste solution containing and discharge cylinder assembly, thereby enabling effective and accurate withdrawal of waste solutions including volatile organic compounds (VOC's).

19 Claims, 2 Drawing Sheets

80
82
3/2 VALVE SOLENOID
84
62
69
64
60
54
58
56
72
68
74
76
66
20
50
70

FIG. 2
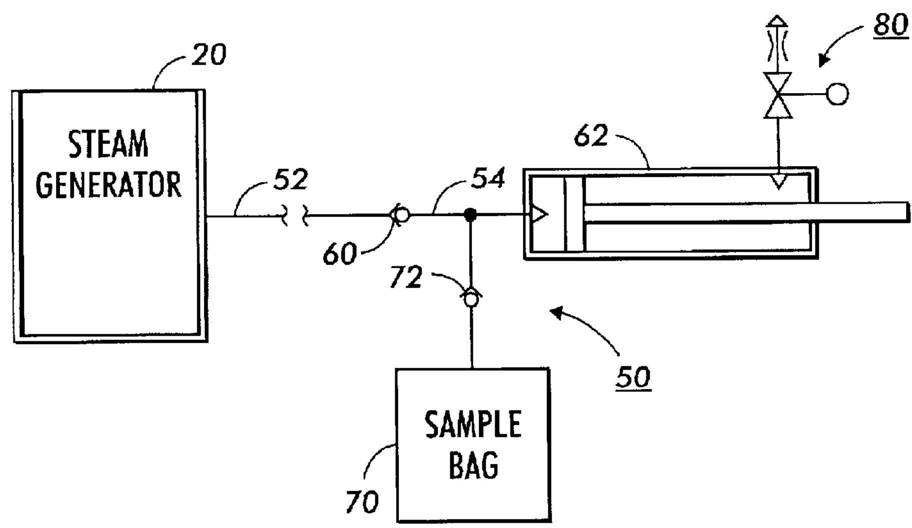
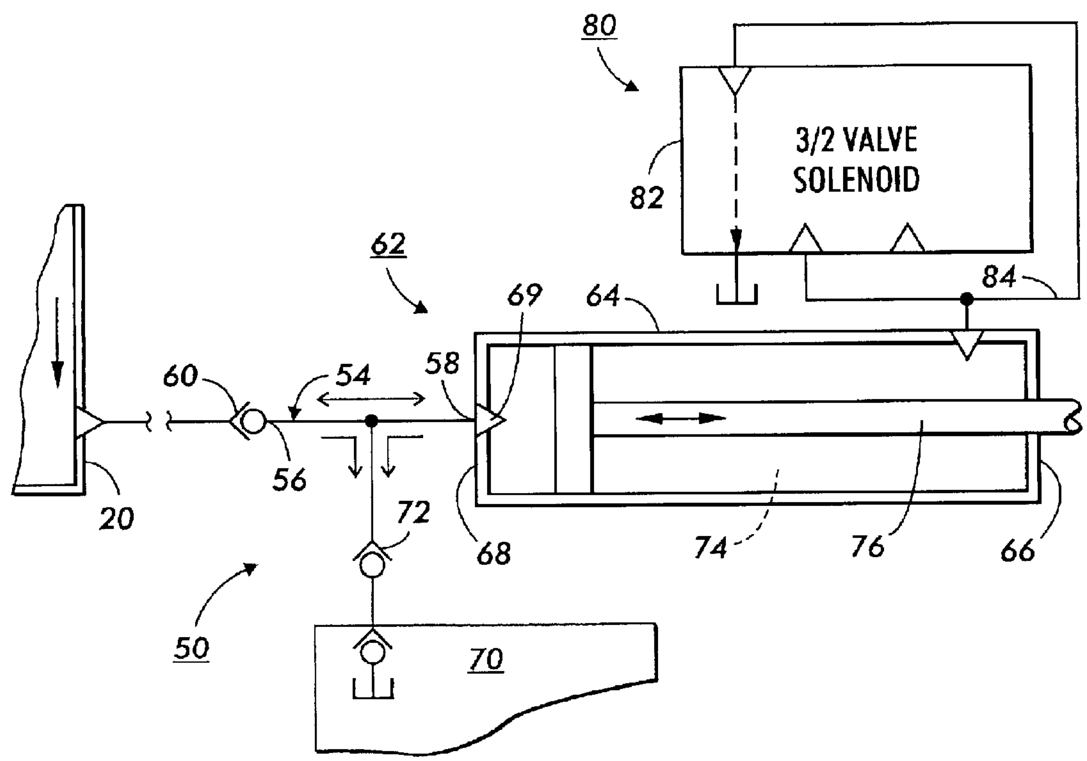
FIG. 3

AIRTIGHT WASTE SOLUTION SAMPLING APPARATUS

BACKGROUND OF THE INVENTION

The present invention relates generally to sampling devices, and more particularly to an airtight waste solution sampling apparatus for effectively and accurately sampling waste treatment solutions that include volatile organic compounds (VOC's).

Many treatment systems have been developed for treating industrial waste or waste from industrial processes in such a manner that the byproducts, after treatment, are suitable for being reused in the process itself, or are otherwise safe for alternate recontainerization or disposal. Typically, each such treatment system will include a Solvent Abatement Carbon Absorbers (SACA) for purifying an industrial waste fluid (air or solution), and a Steam Generator for regenerating the SACA by pumping steam through it.

Unfortunately, solids invariably accumulate at various points within the system including the bottom of the Steam Generator. To prevent transfer of such solids to the SACA, the Steam Generator periodically has to undergo what is called a "blowdown" process during which very hot water and steam are blown downwards through the bottom of the Steam Generator as blowdown waste. This blowdown waste may or may not be acceptable under existing regulatory standards for discharge into the local sanitary sewer.

To be sure existing regulatory standards are satisfied, sampling is usually required. Before sampling however, the blowdown waste must first be isolated and temporarily held or contained, and samples taken from it as such. Permits from regulatory agencies are usually required. Such regulatory agencies are generally reluctant to permit any discharge of waste in some areas, particularly where treatment efficiencies and discharge characteristics are not well-defined. Permitting agencies may prohibit any discharge from a treatment system until the discharge is characterized and shown to be within allowable standards.

Conventionally such samples, for example, are taken from the container or the temporarily held blowdown waste by inserting a dip tube and drawing the sample out. The drawn sample is then poured into an open bottle and capped off. The bottle is then taken to the testing and analytical station for analysis of the contents of the blowdown waste. The regulatory standards are drawn at and are looking for traces of hazardous compounds at levels of Parts per Billion (PPB). The sampling must therefore be precise and accurate in capturing and allowing testing of every compound in the blowdown waste at the very level at which such compound occurs in the waste.

With conventional sampling methods, such precision and accuracy are however a significant problem when the blowdown waste includes volatile organic compounds (VOC's). The main problem in such cases is that the VOC's are unfortunately allowed to escape during the sample collection process. As such, conventional sampling methods do not provide a composite and accurate sample that would represent accurately the blowdown solution being discharged.

There is therefore a need for a volatile compound airtight sampling apparatus for use with waste treatment systems.

SUMMARY OF THE INVENTION

In accordance with the present invention, there is provided an airtight sampling apparatus for effectively and accurately sampling a waste solution including volatile organic compounds (VOC's) from a main waste solution conduit having a first pressure P1, is provided. The airtight sampling apparatus includes (a) a waste solution sampling conduit having a first end and a second end; (b) an input check valve connecting the first end of the waste solution sampling conduit to the main waste solution conduit; (c) an actuatable waste solution containing and discharge cylinder assembly having a first end and a second end connected to the second end of the waste solution sampling conduit; (d) an attachable and removable airtight sample holding container; and (e) a pressure adjustable output valve for coupling to the airtight sample holding container, the pressure adjustable output valve being located between the input check valve and the second end of the waste solution containing and discharge cylinder assembly, thereby enabling effective and accurate withdrawal of waste solutions including volatile organic compounds (VOC's).

BRIEF DESCRIPTION OF THE DRAWINGS

In the detailed description of the invention presented below, reference is made to the drawings, in which:

FIG. 2 is an enlarged schematic of a portion of the system of FIG. 1 and the volatile compound airtight sampling apparatus of the present invention; and FIG. 3 is a detailed illustration of the volatile compound airtight sampling apparatus of the present invention.

DETAILED DESCRIPTION OF THE INVENTION

Figure 1:
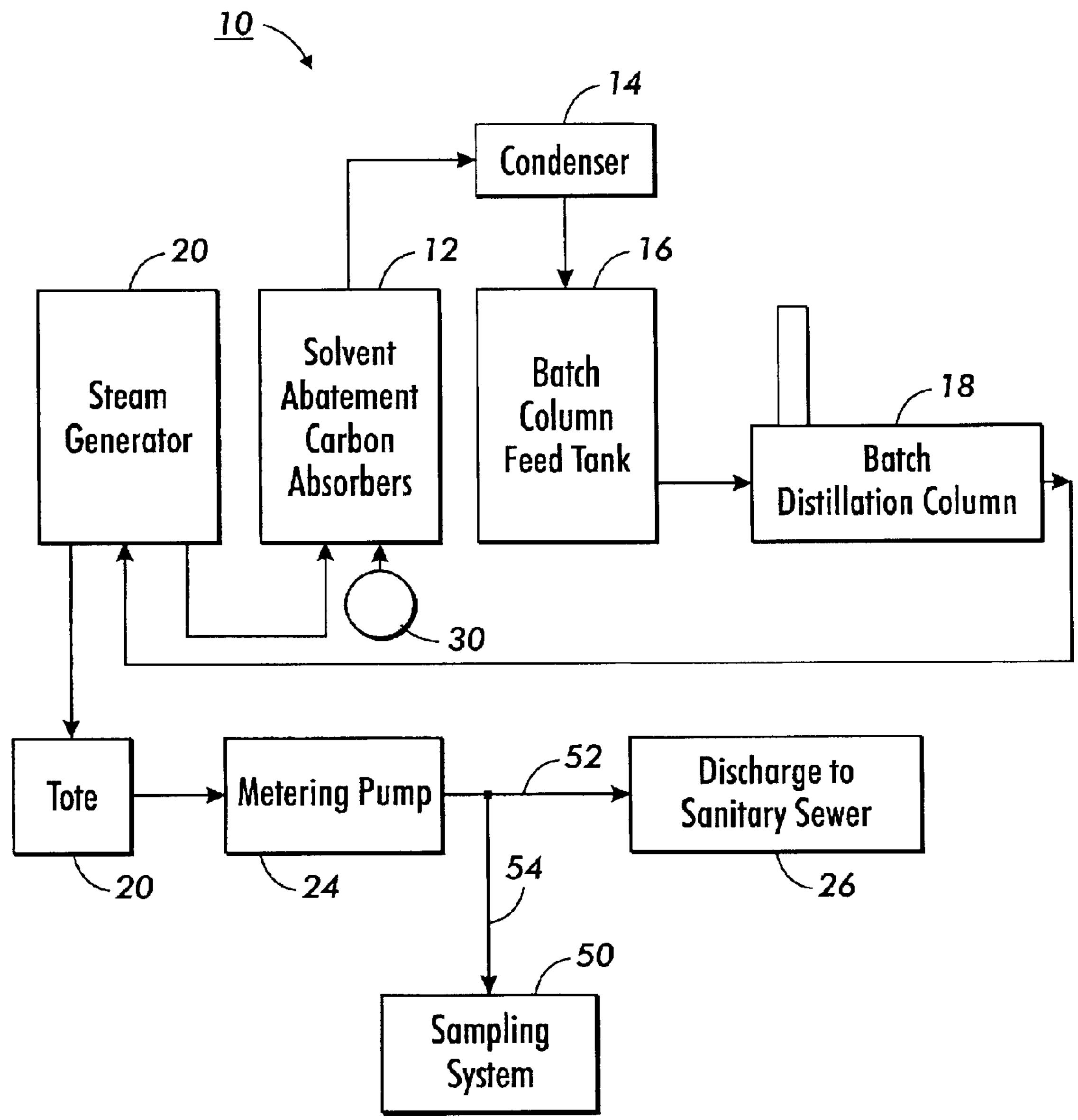
FIG. 1 is a schematic illustration of an exemplary industrial waste treatment system including the volatile compound airtight sampling apparatus of the present invention.

While this invention has been described in conjunction with a particular embodiment thereof, it shall be evident that many alternatives, modifications and variations will be apparent to those skilled in the art. Accordingly, the present invention is intended to embrace all such alternatives, modifications and variations as fall within the spirit and broad scope of the appended claims.

Referring now to FIG. 1, there is illustrated an exemplary industrial waste treatment system 10 including the sampling apparatus 50 of the present invention. As shown, the system 10 includes, for example, at least one Solvent Abatement Carbon Adsorber (SACA) 12, a condenser 14, a Batch Column Feed tank 16, a Batch Distillation Column 18, and a Steam generator 20.

As further shown, the system 10 includes a blowdown solution container such as a tote 22, a metering pump 24, and the volatile compound sampling apparatus 50 of the present invention. When successful treatment is achieved, the blowdown solution can be pumped and is charged as shown into a sanitary sewer system 26.

The SACA 12 is used for purifying a solvent laden fluid 30, for example air, coming from an industrial process such as a coating process. The adsorbers in the SACA 12 are thereafter regenerated when steam from the steam generator 20 is pumped through them. The pumped steam captures, and becomes saturated with, the solvents that had already been absorbed. The solvent saturated steam is thereafter passed through a Condenser 14, where it is condensed into a distillate. The condenser distillate is then captured in the batch column feed tank 16, and ultimately is pumped into the batch distillation column 18 where the solvents are distilled off. As shown, the water that remains after such distillation is pumped back to the steam generator 20 in a closed loop manner.

This closed loop system ordinarily results in an accumulation of solids at the bottom of the steam generator. In order to prevent any of such solids from being transferred to the adsorbers of the SACA 12 during the regeneration process, such solids therefore have to be removed. This is achieved through a periodic blowdown from the steam generator 20. In some systems, the blowdown waste or water typically contains low levels, parts per billion, (PPB) of volatile organic compounds, VOC's.

As pointed out above, the blowdown waste may or may not be acceptable under existing regulatory standards for discharge into the local sanitary sewer. Therefore to be sure existing regulatory standards are satisfied, sampling is usually required. Before sampling however, the blowdown waste must first be isolated and temporarily held or contained for example in an airtight tote 22 from which it is then pumped at a controlled rate by a metering pump 24 into the sanitary sewer, if within regulatory standards. To be sure that it within regulatory standards, samples are taken from it using the airtight waste solution sampling apparatus 50 of the present invention.

Referring now to FIGS. 1–3, the airtight sampling apparatus 50 of the present invention is shown in detail, and is suitable for sampling a waste solution that includes volatile organic compounds (VOC's), from a main waste solution conduit 52 having a first pressure P1. The airtight sampling apparatus 50 includes a waste solution sampling conduit 54 having a first end 56 and a second end 58; an input check valve 60 connecting the first end 56 of the waste solution sampling conduit 54 to the main waste solution conduit 52; and an actuatable waste solution containing and discharge cylinder assembly 62. The actuatable waste solution containing and discharge cylinder assembly 62 includes and air cylinder 64 having a first end 66, and a second end 68 connected to the second end 58 of the waste solution sampling conduit 54.

The airtight sampling apparatus 50 further includes an attachable and removable airtight sample holding container 70; and a pressure adjustable output check valve 72 for coupling to the airtight sample holding container 70. The pressure adjustable output check valve 72 is located between the input check valve 60 and the second end 68 of the air cylinder 64 as, thereby enabling an effective and accurate withdrawal of waste solutions including volatile organic compounds (VOC's) from the main waste solution conduit 52.

The input check valve 60 has a second pressure rating P2 that is less than the first pressure P1 of the main waste solution conduit 52. The second pressure rating P2 is at least 5 PSI less than the first pressure P1. In one embodiment, the second pressure rating P2 is 8 PSI less than the first pressure P1. The pressure adjustable output check valve 72, for example, is a needle valve, and has a third pressure rating P3 that is greater than the second pressure rating P2 of the input check valve 60. The adjustable output check valve 72 can be adjusted so as to allow solution from the sampling conduit 54 to enter the cylinder 62 and not the sample bag 70.

The actuatable waste solution containing and discharge cylinder assembly 62 includes a cylinder 64 having a waste solution containing chamber 74, and a moveable plunger 76 for varying a volume of the waste solution containing chamber 74. The plunger includes TEFLON seals in order to maintain compatibility with the chemical composition of the blowdown solutions.

The actuatable waste solution containing and discharge cylinder assembly 62 also includes instrument air means 80 connected to the air cylinder 64 for controllably moving the plunger 76 back and forth within the air cylinder 64. The instrument air means 80 include an actuatable solenoid valve 82 that is a three-way for inletting and exhausting pressurized air into the air cylinder 64. The instrument air means also include a pressurized air supply 84 for supplying air having a pressure within a range of 40–80 PSI. In an embodiment, the output check valve 72 was sized to be at least 10 psi lower than the instrument air pressure.

To recap, the airtight sampling apparatus 50 of the present invention advantageously enables the extraction of a water sample containing Volatile Organic Compounds (VOC's) such as Methylene Chloride and other organic vapors, without allowing the volatiles to escape to the atmosphere. The airtight sampling apparatus 50 of the present invention for example consists of an air cylinder 64, such as a BIMBA air cylinder, a 1 psi input check valve 60 on the input end 56, and an adjustable pressure 25 psi output check valve 72 on the output end 58 of a waste solution sampling conduit 54. The pressure P1 in the process or main waste solution conduit 52 is about 9 psi, which is enough to overcome the inlet 1 psi check valve, and thus fill the chamber 74 of the air cylinder 64 with an accurate representative sample.

To discharge the representative sample from the cylinder 64, 40–80 psi instrument air is applied to the cylinder 64 to move the plunger 76, thereby causing the sample solution within the chamber 74 to close the overcome the 25 psi output check valve 72, and thus deposit such sample into an airtight container 70, such as an airtight TEDLAR bag. Thus in operation, when the instrument air solenoid 82 is actuated, the instrument air is forced into the air cylinder behind the plunger 76, thus moving the plunger frontward and forcing the sample blowdown waste solution from the chamber 74, through the output check valve 72, and into the airtight container or TEDLAR bag 70.

A needle valve 69 on the exhaust port of the BIMBA air cylinder can be adjusted to restrict the exhaust air flow allowing control of the cylinder fill rate.

As can be seen, there has been provided an airtight sampling apparatus for effectively and accurately sampling a waste solution including volatile organic compounds (VOC's) from a main waste solution conduit having a first pressure P1, is provided. The airtight sampling apparatus includes (a) a waste solution sampling conduit having a first end and a second end; (b) an input check valve connecting the first end of the waste solution sampling conduit to the main waste solution conduit; (c) an actuatable waste solution containing and discharge cylinder assembly having a first end and a second end connected to the second end of the waste solution sampling conduit; (d) an attachable and removable airtight sample holding container; and (e) a pressure adjustable output valve for coupling to the airtight sample holding container, the pressure adjustable output valve being located between the input check valve and the second end of the waste solution containing and discharge cylinder assembly, thereby enabling an effective and accurate withdrawal of waste solutions including volatile organic compounds (VOC's).

While this invention has been described in conjunction with a particular embodiment thereof, it shall be evident that many alternatives, modifications and variations will be apparent to those skilled in the art. Accordingly, the present invention is intended to embrace all such alternatives, modifications and variations as fall within the spirit and broad scope of the appended claims.

What is claimed is:

1. An airtight sampling apparatus for sampling a waste solution including volatile organic compounds (VOC's) from a main waste solution conduit having a first pressure P1, the airtight sampling apparatus comprising:

(a) a waste solution sampling conduit having a first end and a second end;

(b) an input check valve connecting said first end of said waste solution sampling conduit to the main waste solution conduit;

(c) an actuatable waste solution containing and discharge cylinder assembly having a first end and a second end connected to said second end of said waste solution sampling conduit, and said actuatable waste solution containing and discharge cylinder assembly including a cylinder having a waste solution containing chamber and a moveable plunger for varying a volume of said waste solution containing chamber;

(d) an attachable and removable airtight sample holding container and (e) a pressure adjustable output valve for coupling to said airtight sample holding container, said pressure adjustable output valve being located between said input check valve and said second end of said waste solution containing and discharge cylinder assembly, thereby enabling an effective and accurate withdrawal of waste solutions Including volatile organic compounds (VOC's).

2. The airtight sampling apparatus of claim 1, wherein said input check valve has a second pressure rating P2 less than said first pressure P1 of the main solution conduit.

3. The airtight sampling apparatus of claim 1, wherein said pressure adjustable output valve has a third pressure rating PS greater than said second pressure rating P2 of said input check valve.

4. The airtight sampling apparatus of claim 2, wherein said second pressure rating P2 is at least 5 PSI less than said first pressure P1.

5. The airtight sampling apparatus of claim 2, wherein said second pressure rating P2 is 8 PSI less than said first pressure P1.

6. The airtight sampling apparatus of claim 2, wherein said pressure adjustable output valve is a needle valve.

7. The airtight sampling apparatus of claim 1, wherein said actuatable waste solution containing and discharge cylinder includes instrument air means connected to said cylinder for controllably moving said plunger.

8. The airtight sampling apparatus of claim 1, wherein said instrument air means include an actuatable solenoid valve.

9. The airtight sampling apparatus of claim 1, wherein said instrument air means include a pressurized air supply having a pressure within a range of 40–80 PSI.

10. A waste treatment system comprising:

(a) a waste solution producing unit for producing a waste solution including volatile organic compounds (VOC's);

(b) waste solution treatment units including a carbon adsorber unit, said waste solution treatment units being connected by conduit to said waste solution producing unit;

(c) a steam generator connected to said carbon adsorber unit for regenerating said carbon adsorber, said steam generator producing a blowdown waste solution; and (d) an airtight sampling apparatus for sampling blowdown waste solution from a main waste solution conduit having a first pressure P1, the airtight sampling apparatus comprising:

(i) a blowdown waste solution sampling conduit having a first end and a second end;

(ii) an input check valve connecting said first end of said blowdown waste solution sampling conduit to the main waste solution conduit;

(iii) an actuatable blowndown waste solution containing and discharge cylinder assembly having a first end and a second end connected to said second end of said blowndown waste solution sampling conduit;

(iv) an attachable and removable airtight sample holding container for holding a blowndown waste solution sample; and (v) a pressure adjustable output valve for coupling to said airtight sample holding container, said pressure adjustable output valve being located between said input check valve and said second end of said blowndown waste solution containing and discharge cylinder assembly, thereby enabling an effective and accurate withdrawal of samples of the blowndown waste solution including volatile organic compounds (VOC's).

11. The waste treatment system of claim 10, wherein said input check valve has a second pressure rating P2 less than said first pressure P1 of the main solution conduit.

12. The waste treatment system of claim 10, wherein said pressure adjustable output valve has a third pressure rating P3 greater than said second pressure rating P2 of said input check valve.

13. The waste treatment system of claim 10, wherein said actuatable waste solution containing and discharge cylinder assembly includes a cylinder having a waste solution containing chamber and a moveable plunger for varying a volume of said waste solution containing chamber.

14. The waste treatment system of claim 10, wherein said second pressure rating P2 is at least 5 PSI less than said first pressure P1.

15. The waste treatment system of claim 1, wherein said second pressure rating P2 is 8 PSI less than said first pressure P1.

16. The waste treatment system of claim 10, wherein said pressure adjustable output valve is a needle valve.

17. The waste treatment system of claim 10, wherein said actuatable waste solution containing and discharge cylinder includes instrument air means connected to said cylinder for controllably moving said plunger.

18. The waste treatment system of claim 10, wherein said instrument air means include an actuatable solenoid valve.

19. The waste treatment system of claim 10, wherein said instrument air means include a pressurized air supply having a pressure within a range of 40–80 PSI.

* * * * *